US008412320B2

(12) United States Patent
Ostroff et al.

(10) Patent No.: US 8,412,320 B2
(45) Date of Patent: *Apr. 2, 2013

(54) NONTRANSVENOUS AND NONEPICARDIAL METHODS OF CARDIAC TREATMENT AND STIMULUS

(75) Inventors: Alan H. Ostroff, San Clemente, CA (US); William J. Rissmann, Coto de Caza, CA (US); Gary P. Mezack, Norco, CA (US); Gust H. Bardy, Seattle, WA (US)

(73) Assignee: Cameron Health, Inc., San Clemente, CA (US)

( * ) Notice: Subject to any disclaimer, the term of this patent is extended or adjusted under 35 U.S.C. 154(b) by 1384 days.

This patent is subject to a terminal disclaimer.

(21) Appl. No.: 11/205,447

(22) Filed: Aug. 17, 2005

(65) Prior Publication Data

US 2005/0277990 A1 Dec. 15, 2005

Related U.S. Application Data

(63) Continuation of application No. 10/015,202, filed on Nov. 5, 2001, now Pat. No. 6,952,610, which is a continuation-in-part of application No. 09/663,607, filed on Sep. 18, 2000, now Pat. No. 6,721,597, and a continuation-in-part of application No. 09/663,606, filed on Sep. 18, 2000, now Pat. No. 6,647,292.

(51) Int. Cl.
*A61N 1/39* (2006.01)
(52) U.S. Cl. ............... 607/5; 607/4; 607/17; 607/119; 607/120; 607/121; 607/122; 607/123
(58) Field of Classification Search .............. 607/4, 5, 607/17, 119–123
See application file for complete search history.

(56) References Cited

U.S. PATENT DOCUMENTS

| 3,593,718 | A | 7/1971 | Krasner et al. |
| 3,653,387 | A | 4/1972 | Ceier |
| 3,707,974 | A | 1/1973 | Raddi |
| 3,710,374 | A | 1/1973 | Kelly |
| 3,713,449 | A | 1/1973 | Mulier |
| 3,911,925 | A | 10/1975 | Tillery, Jr. |
| 4,157,720 | A | 6/1979 | Greatbatch |
| 4,191,942 | A | 3/1980 | Long |
| 4,223,678 | A | 9/1980 | Langer et al. |
| 4,248,237 | A | 2/1981 | Kenny |
| 4,290,430 | A | 9/1981 | Bihn et al. |
| 4,291,707 | A | 9/1981 | Heilman et al. |
| 4,314,095 | A | 2/1982 | Moore et al. |

(Continued)

FOREIGN PATENT DOCUMENTS

| DE | 298 01 807 U1 | 7/1998 |
| EP | 0 095 727 A1 | 12/1983 |

(Continued)

OTHER PUBLICATIONS

Preliminary Amendment; filed Apr. 18, 2005; U.S. Appl. No. 10/949,877; Heinrich, et al.

(Continued)

*Primary Examiner* — Rex R Holmes
(74) *Attorney, Agent, or Firm* — Schwegman Lundberg & Woessner, P.A.

(57) ABSTRACT

A power supply for an implantable cardioverter-defibrillator for subcutaneous positioning between the third rib and the twelfth rib and using a lead system that does not directly contact a patient's heart or reside in the intrathoracic blood vessels and for providing anti-tachycardia pacing energy to the heart, comprising a capacitor subsystem for storing the anti-tachycardia pacing energy for delivery to the patient's heart; and a battery subsystem electrically coupled to the capacitor subsystem for providing the anti-tachycardia pacing energy to the capacitor subsystem.

17 Claims, 10 Drawing Sheets

U.S. PATENT DOCUMENTS

| | | | |
|---|---|---|---|
| 4,402,322 A | 9/1983 | Duggan | |
| 4,406,286 A | 9/1983 | Stein | |
| 4,407,288 A | 10/1983 | Langer et al. | |
| 4,424,818 A | 1/1984 | Doring et al. | |
| 4,450,527 A | 5/1984 | Sramek | |
| 4,543,956 A | 10/1985 | Herscovici | |
| 4,567,900 A | 2/1986 | Moore | |
| 4,602,637 A | 7/1986 | Elmqvist et al. | |
| 4,603,705 A | 8/1986 | Speicher et al. | |
| 4,693,253 A | 9/1987 | Adams | |
| 4,765,341 A | 8/1988 | Mower et al. | |
| 4,800,883 A | 1/1989 | Winstrom | |
| 4,830,005 A | 5/1989 | Woskow | |
| 4,878,497 A | 11/1989 | Callaghan et al. | |
| 4,944,300 A | 7/1990 | Saksena | |
| 5,105,810 A | 4/1992 | Collins et al. | |
| 5,109,842 A | 5/1992 | Adinolfi | |
| 5,129,392 A | 7/1992 | Bardy et al. | |
| 5,133,353 A | 7/1992 | Hauser | |
| 5,144,946 A | 9/1992 | Weinberg et al. | |
| 5,170,784 A | 12/1992 | Ramon et al. | |
| 5,184,616 A | 2/1993 | Weiss | |
| 5,191,901 A | 3/1993 | Dahl et al. | |
| 5,203,348 A | 4/1993 | Dahl et al. | |
| 5,230,337 A | 7/1993 | Dahl et al. | |
| 5,255,692 A | 10/1993 | Neubauer et al. | |
| 5,261,400 A | 11/1993 | Bardy | |
| 5,265,623 A * | 11/1993 | Kroll et al. | 607/122 |
| 5,300,106 A | 4/1994 | Dahl et al. | |
| 5,318,591 A | 6/1994 | Causey, III et al. | |
| 5,331,966 A | 7/1994 | Bennett et al. | |
| 5,342,400 A * | 8/1994 | Hirschberg et al. | 607/5 |
| 5,342,407 A * | 8/1994 | Dahl et al. | 607/129 |
| 5,366,485 A | 11/1994 | Kroll et al. | |
| 5,366,496 A | 11/1994 | Dahl et al. | |
| 5,376,103 A | 12/1994 | Anderson et al. | |
| 5,376,104 A | 12/1994 | Sakai et al. | |
| 5,385,574 A | 1/1995 | Hauser et al. | |
| 5,391,191 A | 2/1995 | Holmstrom | |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,441,518 A | 8/1995 | Adams et al. | |
| 5,476,503 A | 12/1995 | Yang | |
| 5,509,923 A | 4/1996 | Middleman et al. | |
| 5,509,928 A | 4/1996 | Acken | |
| 5,514,160 A | 5/1996 | Kroll et al. | |
| 5,522,853 A | 6/1996 | Kroll | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,597,956 A | 1/1997 | Ito et al. | |
| 5,601,607 A | 2/1997 | Adams | |
| 5,603,732 A | 2/1997 | Dahl et al. | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,321 A | 8/1997 | Fayram et al. | |
| 5,674,260 A | 10/1997 | Weinberg | |
| 5,690,648 A | 11/1997 | Fogarty et al. | |
| 5,690,683 A | 11/1997 | Haefner et al. | |
| 5,697,953 A | 12/1997 | Kroll et al. | |
| 5,713,926 A | 2/1998 | Hauser et al. | |
| 5,766,226 A | 6/1998 | Pedersen | |
| 5,776,169 A | 7/1998 | Schroeppel | |
| 5,800,464 A | 9/1998 | Kieval | |
| 5,814,090 A | 9/1998 | Latterell et al. | |
| 5,836,976 A | 11/1998 | Min et al. | |
| 5,895,414 A | 4/1999 | Sanchez-Zambrano | |
| 5,919,211 A | 7/1999 | Adams | |
| 5,919,222 A | 7/1999 | Hjelle et al. | |
| 5,925,069 A | 7/1999 | Graves et al. | |
| 5,935,154 A | 8/1999 | Westlund | |
| 5,941,904 A | 8/1999 | Johnston et al. | |
| 5,964,787 A | 10/1999 | Kerver et al. | |
| 5,968,079 A * | 10/1999 | Warman et al. | 607/5 |
| 6,014,586 A | 1/2000 | Weinberg et al. | |
| 6,026,325 A | 2/2000 | Weinberg et al. | |
| 6,058,328 A | 5/2000 | Levine et al. | |
| 6,093,173 A | 7/2000 | Balceta et al. | |
| 6,095,987 A | 8/2000 | Shmulewitz et al. | |
| H1905 H | 10/2000 | Hill | |
| 6,128,531 A | 10/2000 | Campbell-Smith | |
| 6,144,866 A | 11/2000 | Miesel et al. | |
| 6,148,230 A | 11/2000 | KenKnight | |
| 6,185,450 B1 | 2/2001 | Seguine et al. | |
| 6,272,379 B1 * | 8/2001 | Fischell et al. | 607/5 |
| 6,411,844 B1 | 6/2002 | Kroll et al. | |
| 6,519,493 B1 | 2/2003 | Florio et al. | |
| 6,647,292 B1 | 11/2003 | Bardy et al. | |
| 6,721,597 B1 | 4/2004 | Bardy et al. | |
| 6,754,528 B2 | 6/2004 | Bardy et al. | |
| 6,778,860 B2 | 8/2004 | Ostroff et al. | |
| 6,788,974 B2 | 9/2004 | Bardy et al. | |
| 6,834,204 B2 | 12/2004 | Ostroff et al. | |
| 6,856,835 B2 | 2/2005 | Bardy et al. | |
| 6,865,417 B2 | 3/2005 | Rissmann et al. | |
| 6,866,044 B2 | 3/2005 | Bardy et al. | |
| 6,927,721 B2 | 8/2005 | Ostroff et al. | |
| 7,181,274 B2 * | 2/2007 | Rissmann et al. | 607/5 |
| 7,774,058 B2 | 8/2010 | Ostroff et al. | |
| 7,774,059 B2 | 8/2010 | Ostroff et al. | |
| 7,813,797 B2 | 10/2010 | Bardy et al. | |
| 7,835,790 B2 | 11/2010 | Ostroff et al. | |
| 2001/0027330 A1 | 10/2001 | Sullivan et al. | |
| 2002/0082658 A1 | 6/2002 | Heinrich et al. | |
| 2004/0215239 A1 | 10/2004 | Favet | |
| 2005/0021093 A1 | 1/2005 | Brown | |
| 2005/0038476 A1 | 2/2005 | Brown | |
| 2005/0107838 A1 | 5/2005 | Lovett | |
| 2005/0119707 A1 | 6/2005 | Hauser | |
| 2005/0131464 A1 | 6/2005 | Heinrich et al. | |
| 2005/0143776 A1 | 6/2005 | Brown | |
| 2006/0015163 A1 | 1/2006 | Brown | |
| 2006/0174898 A1 | 8/2006 | Brown | |
| 2007/0055314 A1 | 3/2007 | Bardy et al. | |
| 2007/0135847 A1 | 6/2007 | Kenknight | |
| 2007/0142865 A1 | 6/2007 | Bardy et al. | |
| 2008/0046014 A1 | 2/2008 | Bardy et al. | |
| 2008/0140139 A1 | 6/2008 | Heinrich et al. | |
| 2010/0228306 A1 | 9/2010 | Bardy et al. | |

FOREIGN PATENT DOCUMENTS

| | | |
|---|---|---|
| EP | 0 316 616 A2 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |

| | | |
|---|---|---|
| WO | WO 02/24275 A3 | 3/2002 |
| WO | WO 02/068046 A1 | 9/2002 |
| WO | WO 03/018121 A2 | 3/2003 |

OTHER PUBLICATIONS

Preliminary Amendment; filed Apr. 11, 2005; U.S. Appl. No. 10/968,889; Brown.
U.S. Appl. No. 60/252,811, filed Nov. 22, 2000; Heinrich, et al.
Response to Office Action; filed Jun. 28, 2007; U.S. Appl. No. 10/870,278; Brown.
U.S. Appl. No. 60/462,272, filed Apr. 11, 2003; Haefner, et al.
Bardy, Gust H. et al., "Multicenter Experience with a Pectoral Unipolar Implantable Cardioverter-Defibrillator," *JACC*, Aug. 1996, vol. 28, No. 2, pp. 400-410.
Friedman, Richard A. et al., "Implantable Defibrillators in Children: From Whence to Shock," *Journal of Cardiovascular Electrophysiology*, vol. 12, No. 3, Mar. 2001, pp. 361-362.
Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.
Higgins, Steven L. et al., "The First Year Experience with the Dual Chamber ICD," *PACE*, Jan. 2000, vol. 23, pp. 18-25.
Mirowski, M. et al., "Automatic Detection and Defibrillation of Lethal Arrhythmias—A New Concept," *JAMA*, vol. 213, No. 4, Jul. 27, 1970, pp. 615-616.
Olson, Walter H. et al., "Onset and Stability for Ventricular Tachyarrhythmia Detection in an Implantable Pacer-Cardioverter-Defribrillator," *IEEE*, (1987) pp. 167-170.
Schuder, John C. et al., "Experimental Ventricular Defibrillation with an Automatic and Completely Implanted System," *Trans. Amer. Soc. Artif. Int. Organs*, vol. XVI (1970) pp. 207-212.
Schuder, John C. et al., "Standby Implanted Defibrillators," *Arch Intern. Med*, vol. 127, Feb. 1971, p. 317 (single sheet).
Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.
Schuder, John C., "Completely Implanted Defribrillator," *JAMA*, vol. 214, No. 6, Nov. 9, 1970. p. 1123 (single sheet).
Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.
Schwacke, H. et al., "Komplikationen mit Sonden bei 340 Patienten mit einem Implantierbaren Kardiovater/Defibrillator," *Z Kardiol* (1999) vol. 88, No. 8, pp. 559-565.
Tietze U. et al., "Halbleiter-Schaltungstechnik," ©Springer-Verlag (Berlin, Germany), (1991), pp. 784-786.
Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.
Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.
Amendment Accompanying RCE (Apr. 2, 2009), Advisory Action (Mar. 20, 2009), Response After Final (Mar. 2, 2009), and Final Office Action (Jan. 2, 2009); U.S. Appl. No. 11/447,531 (US 2006-0229682 A1—Rissmann, et al).
Response/Amendment (Feb. 22, 2011), Office Action (Aug. 23, 2010), Response/Amendment (Jun. 16, 2010), Restriction Requirement (Dec. 17, 2009), and Preliminary Amendment (Feb. 15, 2008); U.S. Appl. No. 11/981,410 (US 2008-0140139 A1—Heinrich, et al.).
Final Action (Jul. 13, 2010), Response/Amendment (Apr. 28, 2010), Interview Summary (Mar. 22, 2010), Restriction Requirement (Dec. 30, 2009), Response/Amendment (Oct. 19, 2009), Supplemental Office Action (Apr. 17, 2009), Interview Summaries (Apr. 16/14, 2009), Office Action (Oct. 17, 2008), Amendment/Response (Jun. 5, 2008), Interview Summary (May 28, 2008), Restriction Requirement (Dec. 6, 2007), and Preliminary Amendment (Apr. 11, 2005); U.S. Appl. No. 10/968,889 (US 2005-0143776 A1—Brown).
RCE, Amendment, and IDS (Feb. 1, 2011)Interview Summary (May 18, 2010), Final Action (Jan. 4, 2010), Response/Amendment (Oct. 19, 2009), Office Action (Apr. 20, 2009), Response/Amendment (Mar. 18, 2009), Interview Summary (Feb. 20, 2009), Restriction Requirement (Sep. 18, 2008), and Preliminary Amendment (Apr. 18, 2005); U.S. Appl. No. 10/949,877 (US 2005-0131464 A1—Heinrich, et al.).
Amendment/Response (Nov. 30, 2010), Office Action (Sep. 1, 2010), Response/Amendment (Jun. 7, 2010), Office Action (Mar. 5, 2010), Response/Amendment (Nov. 30, 2009), and Restriction Requirement (Oct. 30, 2009); U.S. Appl. No. 11/877,323 (US 2008-0046014 A1—Bardy, et al.).
RCE and Amendment (Jul. 16, 2010), Advisory Action (Jul. 2, 2010), Response/Amendment after Final (Jun. 16, 2010), Final Action (Apr. 16, 2010), Response/Amemdment (Dec. 16, 2009), Office Action (Sep. 17, 2009), Response/Amendment (Jul. 2, 2009), and Restriction Requirement (Jun. 5, 2009); U.S. Appl. No. 11/680,107 (US 2007-0142865 A1—Bardy, et al.).
RCE and Amendment (Feb. 25, 2010), Advisory Action (Jan. 25, 2010), Response/Amendment after Final (Dec. 15, 2009), Final Action (Oct. 15, 2009), Response/Amendment (Jun. 19, 2009), and Office Action (Mar. 19, 2009); U.S. Appl. No. 11/554,185 (US 2007-0055314 A1—Bardy, et al.).

\* cited by examiner

NONTRANSVENOUS AND NONEPICARDIAL METHODS OF CARDIAC TREATMENT AND STIMULUS

CROSS-REFERENCE TO RELATED APPLICATIONS

This application is a continuation of U.S. patent application Ser. No. 10/015,202, filed Nov. 5, 2001, titled CURRENT WAVEFORMS FOR ANTI-TACHYCARDIA PACING FOR A SUBCUTANEOUS IMPLANTABLE CARDIOVERTER-DEFIBRILLATOR, now U.S. Pat. No. 6,952,610; which is a continuation-in-part of U.S. patent application Ser. No. 09/663,607, filed Sep. 18, 2000, titled SUBCUTANEOUS ONLY IMPLANTABLE CARDIOVERTER-DEFIBRILLATOR AND OPTIONAL PACER, now U.S. Pat. No. 6,721,597; and U.S. patent application Ser. No. 09/663,606, filed Sep. 18, 2000, titled UNITARY SUBCUTANEOUS ONLY IMPLANTABLE CARDIOVERTER-DEFIBRILLATOR AND OPTIONAL PACER, now U.S. Pat. No. 6,647,292; the entire disclosures of which are all incorporated herein by reference.

In addition, the present application is related to U.S. patent application Ser. No. 10/011,860, filed Nov. 5, 2001, titled MONOPHASIC WAVEFORM FOR ANTI-BRADYCARDIA PACING FOR A SUBCUTANEOUS IMPLANTABLE CARDIOVERTER-DEFIBRILLATOR, now U.S. Pat. No. 7,092,754; U.S. patent application Ser. No. 10/011,958, filed Nov. 5, 2001, titled MONOPHASIC WAVEFORM FOR ANTI-TACHYCARDIA PACING FOR A SUBCUTANEOUS IMPLANTABLE CARDIOVERTER-DEFIBRILLATOR, published as US 2002-0095184 A1; and U.S. patent application Ser. No. 10/011,506, filed Nov. 5, 2001, titled CURRENT WAVEFORMS FOR ANTI-BRADYCARDIA PACING FOR A SUBCUTANEOUS CARDIOVERTER DEFIBRILLATOR, published as US 2002-0107544 A1; the disclosures of which are all incorporated herein by reference.

FIELD OF THE INVENTION

The present invention relates to an apparatus and method for performing electrical cardioversion/defibrillation and optional pacing of the heart via a totally subcutaneous nontransvenous system.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing. Shocks used for defibrillation therapy can comprise a biphasic truncated exponential waveform. As for pacing, a constant current density is desired to reduce or eliminate variability due to the electrode/tissue interface Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava and, into one or more endocardial areas of the heart. Such electrode systems are called intravascular or transvenous electrodes. U.S. Pat. Nos. 4,603,705; 4,693,253; 4,944,300; and 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400; 5,620,477; and 5,658,321, the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5-10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

SUMMARY OF THE INVENTION

A power supply for an implantable cardioverter-defibrillator for subcutaneous positioning between the third rib and the twelfth rib and using a lead system that does not directly contact a patient's heart or reside in the intrathoracic blood vessels and for providing anti-tachycardia pacing energy to the heart, comprising a capacitor subsystem for storing the anti-tachycardia pacing energy for delivery to the patient's heart; and a battery subsystem electrically coupled to the capacitor subsystem for providing the anti-tachycardia pacing energy to the capacitor subsystem.

BRIEF DESCRIPTION OF THE DRAWINGS

For a better understanding of the invention, reference is now made to the drawings where like numerals represent similar objects throughout the figures where.

DETAILED DESCRIPTION

Figure 1:
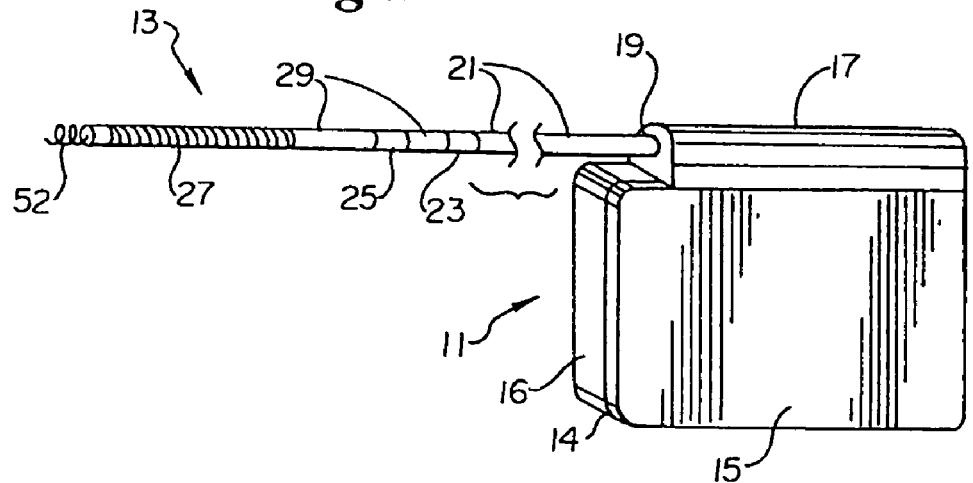
FIG. 1 is a schematic view of a subcutaneous ICD (S-ICD) of the present invention.

Turning now to FIG. 1, the S-ICD of the present invention is illustrated. The S-ICD consists of an electrically active canister 11 and a subcutaneous electrode 13 attached to the canister. The canister has an electrically active surface 15 that is electrically insulated from the electrode connector block 17 and the canister housing 16 via insulating area 14. The canister can be similar to numerous electrically active canisters commercially available in that the canister will contain a battery supply, capacitor and operational circuitry. Alternatively, the canister can be thin and elongated to conform to the intercostal space. The circuitry will be able to monitor cardiac rhythms for tachycardia and fibrillation, and if detected, will initiate charging the capacitor and then delivering cardioversion/defibrillation energy through the active surface of the housing and to the subcutaneous electrode. Examples of such circuitry are described in U.S. Pat. Nos. 4,693,253 and 5,105,810, the entire disclosures of which are herein incorporated by reference. The canister circuitry can provide cardioversion/defibrillation energy in different types of waveforms. In one embodiment, a 100 uF biphasic waveform is used of approximately 10-20 ms total duration and with the initial phase containing approximately ⅔ of the energy, however, any type of waveform can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the active surface and the subcutaneous electrode. Pacing stimuli can be biphasic in one embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of atrial fibrillation as described in Olson, W. et al. "Onset And Stability For Ventricular Tachyarrhythmia Detection in an Implantable Cardioverter and Defibrillator," Computers in Cardiology (1986) pp. 167-170. Detection can be provided via R-R Cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form, a rate detection algorithm that triggers charging of the capacitor once the ventricular rate exceeds some predetermined level for a fixed period of time: for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R-R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patent is not respiring and this lack of respiration can be used to confirm the QRS findings of cardiac arrest. The same technique can be used to provide information about the respiratory rate or estimate cardiac output as described in U.S. Pat. Nos. 6,095,987; 5,423,326; and 4,450,527, the entire disclosures of which are incorporated herein by reference.

The canister of the present invention can be made out of titanium alloy or other presently preferred electrically active canister designs. However, it is contemplated that a malleable canister that can conform to the curvature of the patient's chest will be preferred. In this way the patient can have a comfortable canister that conforms to the shape of the patient's rib cage. Examples of conforming canisters are provided in U.S. Pat. No. 5,645,586, the entire disclosure of which is herein incorporated by reference. Therefore, the canister can be made out of numerous materials such as medical grade plastics, metals, and alloys. In the preferred embodiment, the canister is smaller than 60 cc volume having a weight of less than 100 gms for long term wearability, especially in children. The canister and the lead of the S-ICD can also use fractal or wrinkled surfaces to increase surface area to improve defibrillation capability. Because of the primary prevention role of the therapy and the likely need to reach energies over 40 Joules, a feature of one embodiment is that the charge time for the therapy, is intentionally left relatively long to allow capacitor charging within the limitations of device size. Examples of small ICD housings are disclosed in U.S. Pat. Nos. 5,597,956 and 5,405,363, the entire disclosures of which are incorporated herein by reference.

Figure 2:
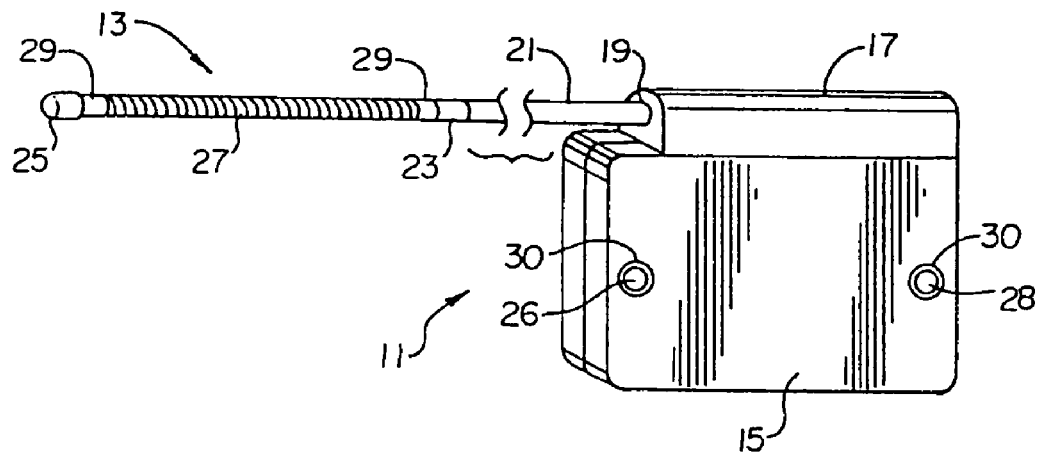
FIG. 2 is a schematic view of an alternate embodiment of a subcutaneous electrode of the present invention.
Figure 3:
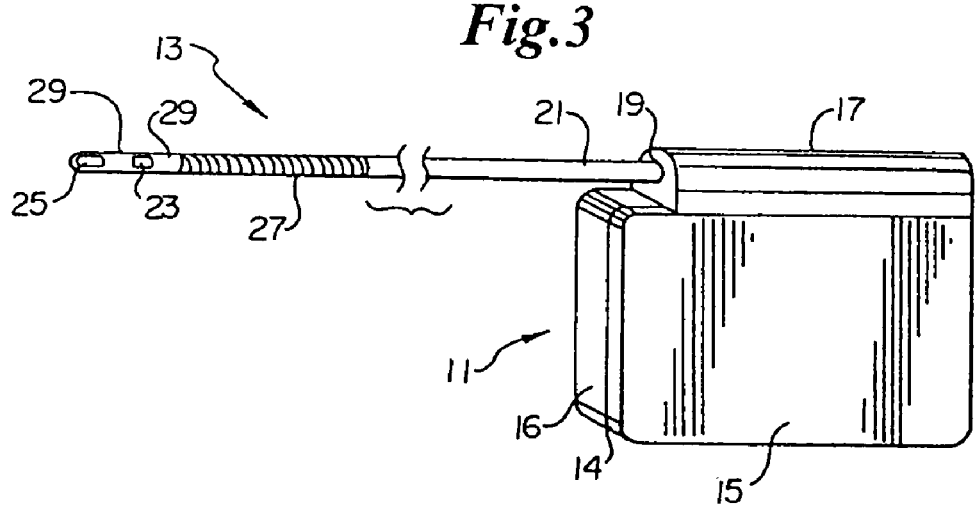
FIG. 3 is a schematic view of an alternate embodiment of a subcutaneous electrode of the present invention.

Different subcutaneous electrodes 13 of the present invention are illustrated in FIGS. 1-3. Turning to FIG. 1, the lead 21 for the subcutaneous electrode is preferably composed of silicone or polyurethane insulation. The electrode is connected to the canister at its proximal end via connection port 19 which is located on an electrically insulated area 17 of the canister. The electrode illustrated is a composite electrode with three different electrodes attached to the lead. In the embodiment illustrated, an optional anchor segment 52 is attached at the most distal end of the subcutaneous electrode for anchoring the electrode into soft tissue such that the electrode does not dislodge after implantation.

The most distal electrode on the composite subcutaneous electrode is a coil electrode 27 that is used for delivering the high voltage cardioversion/defibrillation energy across the heart. The coil cardioversion/defibrillation electrode is about 5-10 cm in length. Proximal to the coil electrode are two sense electrodes, a first sense electrode 25 is located proximally to the coil electrode and a second sense electrode 23 is located proximally to the first sense electrode. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 29. Similar types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is illustrated in FIG. 2 where the two sensing electrodes 25 and 23 are non-circumferential sensing electrodes and one is located at the distal end, the other is located proximal thereto with the coil electrode located in between the two sensing electrodes. In this embodiment the sense electrodes are spaced about 6 to about 12 cm apart depending on the length of the coil electrode used. FIG. 3 illustrates yet a further embodiment where the two sensing electrodes are located at the distal end to the composite electrode with the coil electrode located proximally thereto. Other possibilities exist and are contemplated within the present invention. For example, having only one sensing electrode, either proximal or distal to the coil cardioversion/defibrillation electrode, with the coil serving as both a sensing electrode and a cardioversion/defibrillation electrode.

It is also contemplated within the scope of the invention that the sensing of QRS waves (and transthoracic impedance) can be carried out via sense electrodes on the canister housing or in combination with the cardioversion/defibrillation coil electrode and/or the subcutaneous lead sensing electrode(s). In this way, sensing could be performed via the one coil electrode located on the subcutaneous electrode and the active surface on the canister housing. Another possibility would be to have only one sense electrode located on the subcutaneous electrode and the sensing would be performed by that one electrode and either the coil electrode on the subcutaneous electrode or by the active surface of the canister. The use of sensing electrodes on the canister would eliminate the need for sensing electrodes on the subcutaneous electrode. It is also contemplated that the subcutaneous electrode would be provided with at least one sense electrode, the canister with at least one sense electrode, and if multiple sense electrodes are used on either the subcutaneous electrode and/or the canister, that the best QRS wave detection combination will be identified when the S-ICD is implanted and this combination can be selected, activating the best sensing arrangement from all the existing sensing possibilities. Turning again to FIG. 2, two sensing electrodes 26 and 28 are located on the electrically active surface 15 with electrical insulator rings 30 placed between the sense electrodes and the active surface. These canister sense electrodes could be switched off and electrically insulated during and shortly after defibrillation/cardioversion shock delivery. The canister sense electrodes may also be placed on the electrically inactive surface of the canister. In the embodiment of FIG. 2, there are actually four sensing electrodes, two on the subcutaneous lead and two on the canister. In the preferred embodiment, the ability to change which electrodes are used for sensing would be a programmable feature of the S-ICD to adapt to changes in the patient physiology and size (in the case of children) over time. The programming could be done via the use of physical switches on the canister, or as presently preferred, via the use of a programming wand or via a wireless connection to program the circuitry within the canister.

The canister could be employed as either a cathode or an anode of the S-ICD cardioversion/defibrillation system. If the canister is the cathode, then the subcutaneous coil electrode would be the anode. Likewise, if the canister is the anode, then the subcutaneous electrode would be the cathode.

The active canister housing will provide energy and voltage intermediate to that available with ICDs and most AEDs. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The S-ICD and the US-ICD of the present invention uses maximum voltages in the range of about 50 to about 3500 Volts and is associated with energies of about 0.5 to about 350 Joules. The capacitance of the devices can range from about 25 to about 200 micro farads.

In another embodiment, the S-ICD and US-ICD devices provide energy with a pulse width of approximately one millisecond to approximately 40 milliseconds. The devices can provide pacing current of approximately one milliamp to approximately 250 milliamps.

The sense circuitry contained within the canister is highly sensitive and specific for the presence or absence of life threatening ventricular arrhythmias. Features of the detection algorithm are programmable and the algorithm is focused on the detection of V-FIB and high rate V-TACH (>240 bpm). Although the S-ICD of the present invention may rarely be used for an actual life-threatening event, the simplicity of design and implementation allows it to be employed in large populations of patients at modest risk with modest cost by non-cardiac electrophysiologists. Consequently, the S-ICD of the present invention focuses mostly on the detection and therapy of the most malignant rhythm disorders. As part of the detection algorithm's applicability to children, the upper rate range is programmable upward for use in children, known to have rapid supraventricular tachycardias and more rapid ventricular fibrillation. Energy levels also are programmable downward in order to allow treatment of neonates and infants.

Figure 4:
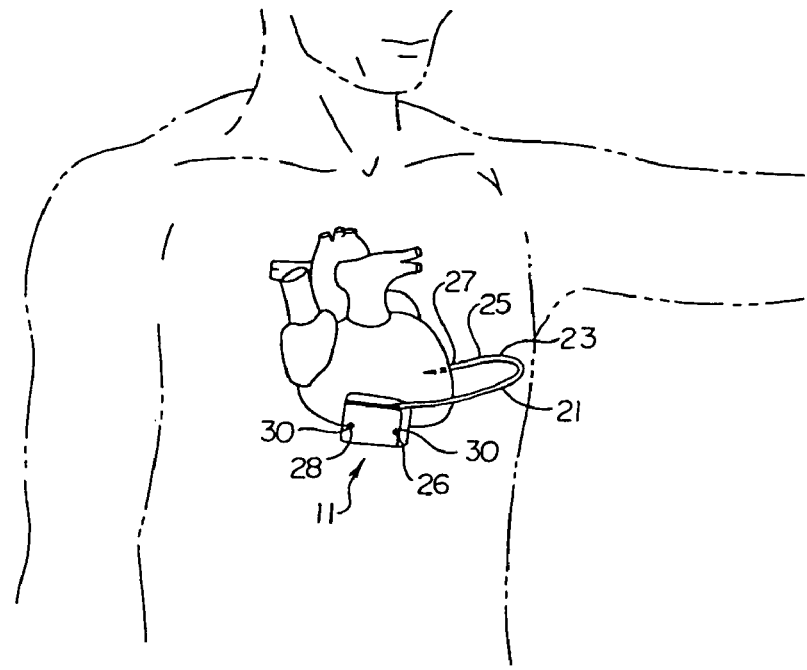
FIG. 4 is a schematic view of the S-ICD and lead of FIG. 1 subcutaneously implanted in the thorax of a patient.

Turning now to FIG. 4, the optimal subcutaneous placement of the S-ICD of the present invention is illustrated. As would be evidence to a person skilled in the art, the actual location of the S-ICD is in a subcutaneous space that is developed during the implantation process. The heart is not exposed during this process and the heart is schematically illustrated in the figures only for help in understanding where the canister and coil electrode are three dimensionally located in the left mid-clavicular line approximately at the level of the inframammary crease at approximately the 5th rib. The lead 21 of the subcutaneous electrode traverses in a subcutaneous path around the thorax terminating with its distal electrode end at the posterior axillary line ideally just lateral to the left scapula. This way the canister and subcutaneous cardioversion/defibrillation electrode provide a reasonably good pathway for current delivery to the majority of the ventricular myocardium.

Figure 5:
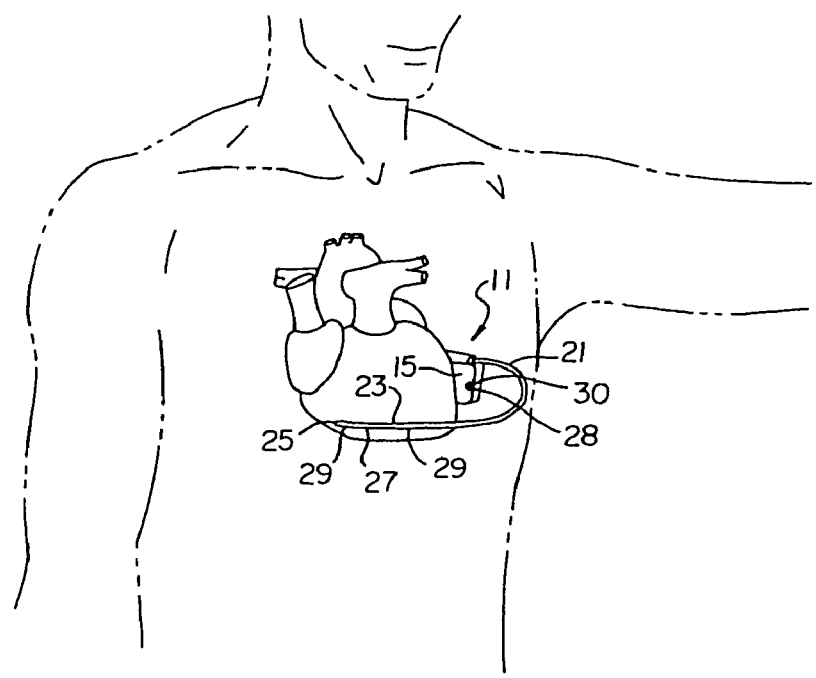
FIG. 5 is a schematic view of the S-ICD and lead of FIG. 2 subcutaneously implanted in an alternate location within the thorax of a patient.
Figure 6:
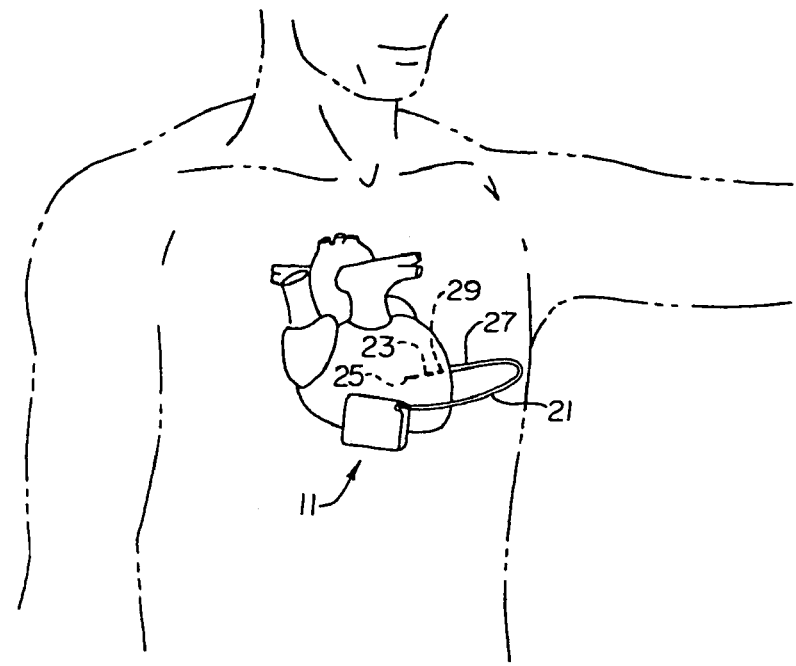
FIG. 6 is a schematic view of the S-ICD and lead of FIG. 3 subcutaneously implanted in the thorax of a patient.

FIG. 5 illustrates a different placement of the present invention. The S-ICD canister with the active housing is located in the left posterior axillary line approximately lateral to the tip of the inferior portion of the scapula. This location is especially useful in children. The lead 21 of the subcutaneous electrode traverses in a subcutaneous path around the thorax terminating with its distal electrode end at the anterior precordial region, ideally in the inframammary crease. FIG. 6 illustrates the embodiment of FIG. 1 subcutaneously implanted in the thorax with the proximal sense electrodes 23 and 25 located at approximately the left axillary line with the cardioversion/defibrillation electrode just lateral to the tip of the inferior portion of the scapula.

Figure 7:
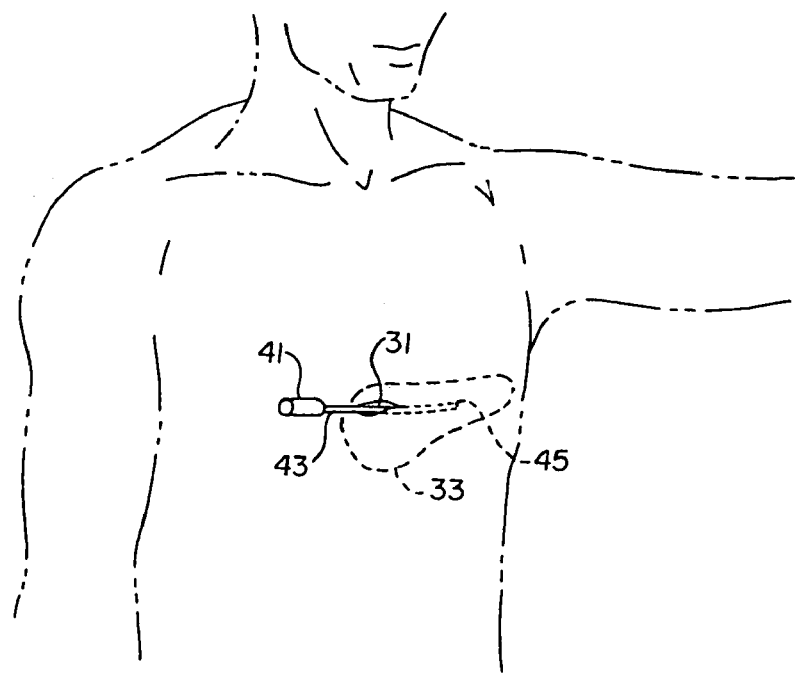
FIG. 7 is a schematic view of the method of making a subcutaneous path from the preferred incision and housing implantation point to a termination point for locating a subcutaneous electrode of the present invention.

FIG. 7 schematically illustrates the method for implanting the S-ICD of the present invention. An incision 31 is made in the left anterior axillary line approximately at the level of the cardiac apex. This incision location is distinct from that chosen for S-ICD placement and is selected specifically to allow both canister location more medially in the left inframammary crease and lead positioning more posteriorly via the introducer set (described below) around to the left posterior axillary line lateral to the left scapula. That said, the incision can be anywhere on the thorax deemed reasonably by the implanting physician although in the preferred embodiment, the S-ICD of the present invention will be applied in this region. A subcutaneous pathway 33 is then created medially to the inframammary crease for the canister and posteriorly to the left posterior axillary line lateral to the left scapula for the lead.

Figure 8:
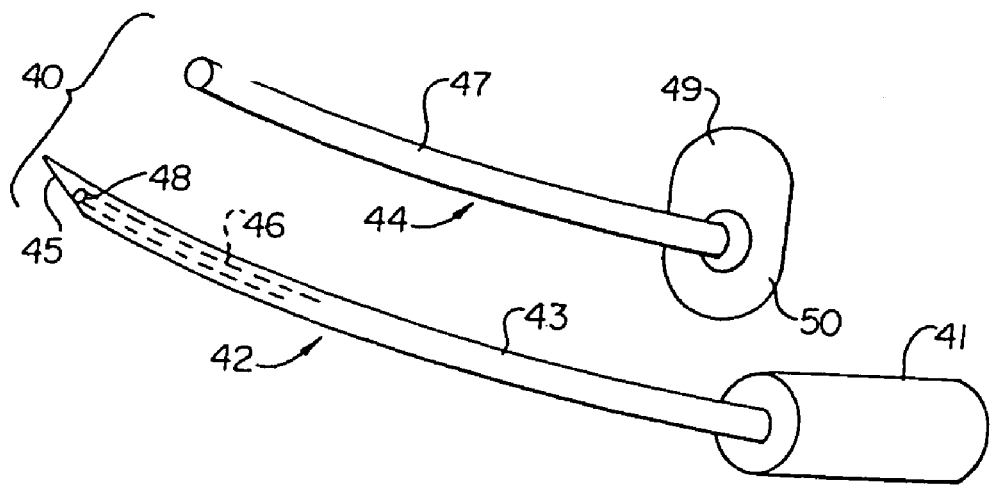
FIG. 8 is a schematic view of an introducer set for performing the method of lead insertion of any of the described embodiments.

The S-ICD canister 11 is then placed subcutaneously at the location of the incision or medially at the subcutaneous region at the left inframammary crease. The subcutaneous electrode 13 is placed with a specially designed curved introducer set 40 (see FIG. 8). The introducer set comprises a curved trocar 42 and a stiff curved peel away sheath 44. The peel away sheath is curved to allow for placement around the rib cage of the patient in the subcutaneous space created by the trocar. The sheath has to be stiff enough to allow for the placement of the electrodes without the sheath collapsing or bending. Preferably the sheath is made out of a biocompatible plastic material and is perforated along its axial length to allow for it to split apart into two sections. The trocar has a proximal handle 41 and a curved shaft 43. The distal end 45 of the trocar is tapered to allow for dissection of a subcutaneous path 33 in the patient. Preferably, the trocar is cannulated having a central Lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. The curved peel away sheath 44 has a proximal pull tab 49 for breaking the sheath into two halves along its axial shaft 47. The sheath is placed over a guidewire inserted through the trocar after the subcutaneous path has been created. The subcutaneous pathway is then developed until it terminates subcutaneously at a location that, if a straight line were drawn from the canister location to the path termination point the line would intersect a substantial portion of the left ventricular mass of the patient. The guidewire is then removed leaving the peel away sheath. The subcutaneous lead system is then inserted through the sheath until it is in the proper location. Once the subcutaneous lead system is in the proper location, the sheath is split in half using the pull tab 49 and removed. If more than one subcutaneous electrode is being used, a new curved peel away sheath can be used for each subcutaneous electrode.

Figure 9:
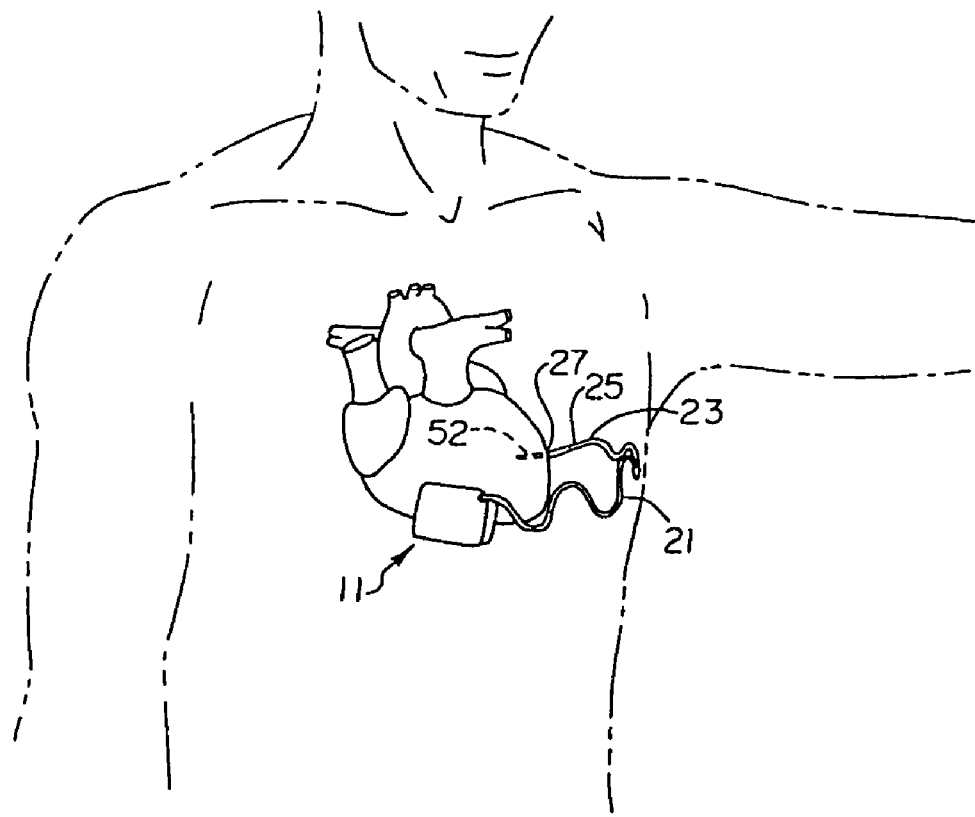
FIG. 9 is a schematic view of an alternative S-ICD of the present invention illustrating a lead subcutaneously and serpiginously implanted in the thorax of a patient for use particularly in children.

The S-ICD will have prophylactic use in adults where chronic transvenous/epicardial ICD lead systems pose excessive risk or have already resulted in difficulty, such as sepsis or lead fractures. It is also contemplated that a major use of the S-ICD system of the present invention will be for prophylactic use in children who are at risk for having fatal arrhythmias, where chronic transvenous lead systems pose significant management problems. Additionally, with the use of standard transvenous ICDs in children, problems develop during patient growth in that the lead system does not accommodate the growth. FIG. 9 illustrates the placement of the S-ICD subcutaneous lead system such that he problem that growth presents to the lead system is overcome. The distal end of the subcutaneous electrode is placed in the same location as described above providing a good location for the coil cardioversion/defibrillation electrode 27 and the sensing electrodes 23 and 25. The insulated lead 21, however, is no longer placed in a taut configuration. Instead, the lead is serpiginously placed with a specially designed introducer trocar and sheath such that it has numerous waves or bends. As the child grows, the waves or bends will straighten out lengthening the lead system while maintaining proper electrode placement. Although it is expected that fibrous scarring especially around the defibrillation coil will help anchor it into position to maintain its posterior position during growth, a lead system with a distal tine or screw electrode anchoring system 52 can also be incorporated into the distal tip of the lead to facilitate lead stability (see FIG. 1). Other anchoring systems can also be used such as hooks, sutures, or the like.

Figure 10:
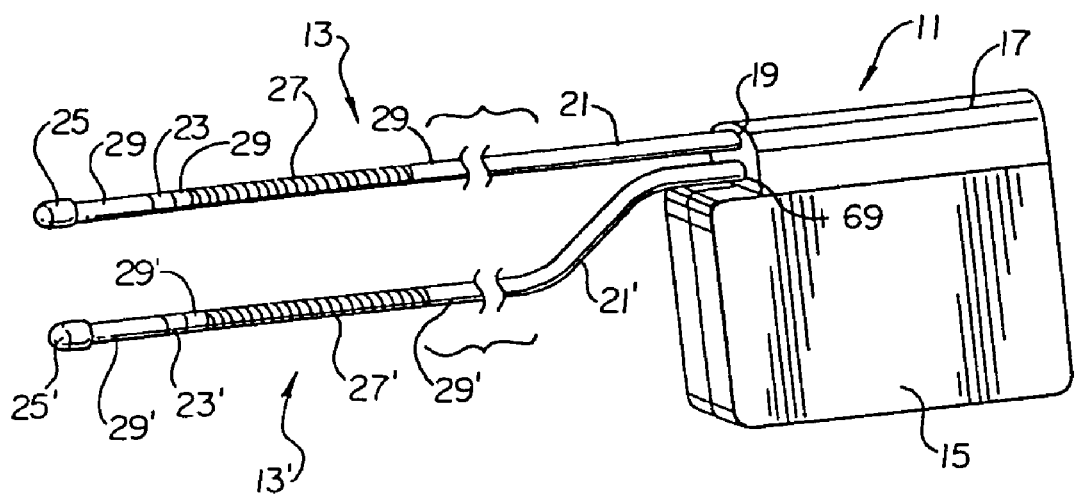
FIG. 10 is a schematic view of an alternate embodiment of an S-ICD of the present invention.
Figure 11:
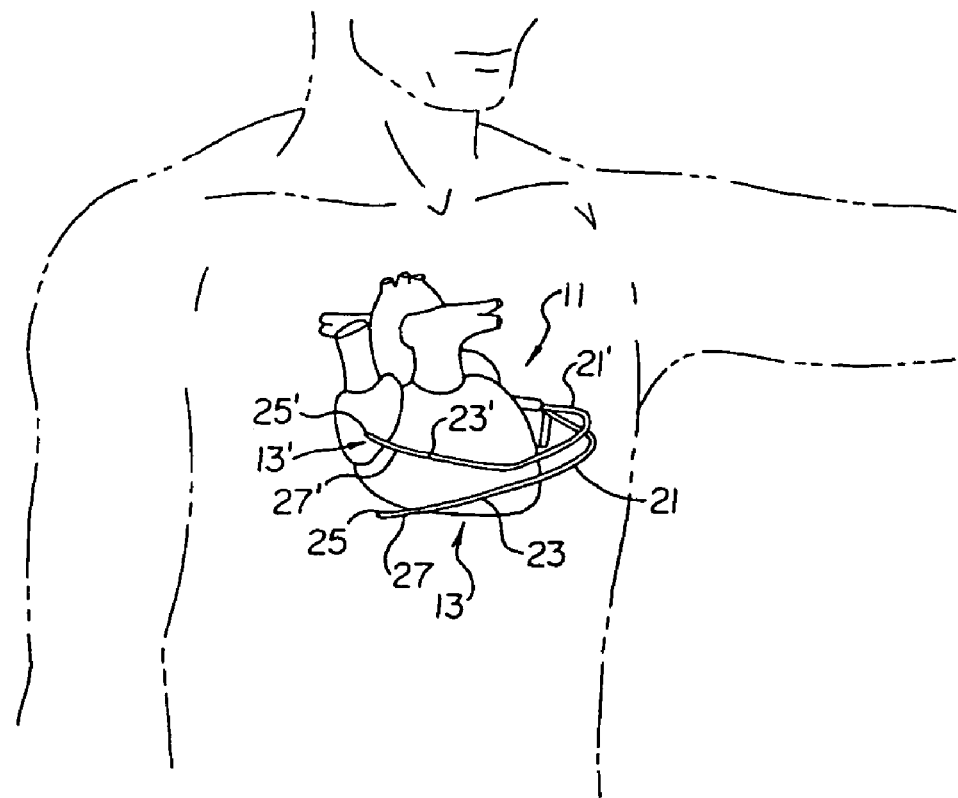
FIG. 11 is a schematic view of the S-ICD of FIG. 10 subcutaneously implanted in the thorax of a patient.

FIGS. 10 and 11 illustrate another embodiment of the present S-ICD invention. In this embodiment there are two subcutaneous electrodes 13 and 13' of opposite polarity to the canister. The additional subcutaneous electrode 13' is essentially identical to the previously described electrode. In this embodiment the cardioversion/defibrillation energy is delivered between the active surface of the canister and the two coil electrodes 27 and 27'. Additionally, provided in the canister is means for selecting the optimum sensing arrangement between the four sense electrodes 23, 23', 25, and 25'. The two electrodes are subcutaneously placed on the same side of the heart. As illustrated in FIG. 6, one subcutaneous electrode 13 is placed inferiorly and the other electrode 13' is placed superiorly. It is also contemplated with this dual subcutaneous electrode system that the canister and one subcutaneous electrode are the same polarity and the other subcutaneous electrode is the opposite polarity.

Figure 12:
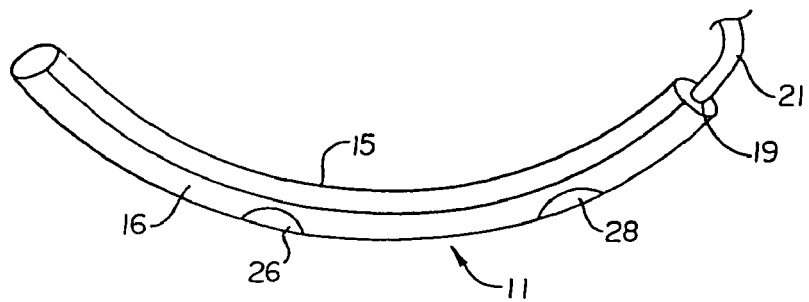
FIG. 12 is a schematic view of yet a further embodiment where the canister of the S-ICD of the present invention is shaped to be particularly useful in placing subcutaneously adjacent and parallel to a rib of a patient.
Figure 13:
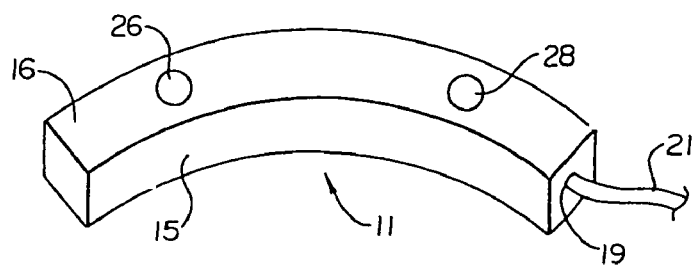
FIG. 13 is a schematic view of a different embodiment where the canister of the S-ICD of the present invention is shaped to be particularly useful in placing subcutaneously adjacent and parallel to a rib of a patient.

Turning now to FIGS. 12 and 13, further embodiments are illustrated where the canister 11 of the S-ICD of the present invention is shaped to be particularly useful in placing subcutaneously adjacent and parallel to a rib of a patient. The canister is long, thin, and curved to conform to the shape of the patient's rib. In the embodiment illustrated in FIG. 12, the canister has a diameter ranging from about 0.5 cm to about 2 cm without 1 cm being presently preferred. Alternatively, instead of having a circular cross sectional area, the canister could have a rectangular or square cross sectional area as illustrated in FIG. 13 without falling outside of the scope of the present invention. The length of the canister can vary depending on the size of the patient's thorax. In an embodiment, the canister is about 5 cm to about 40 cm long. The canister is curved to conform to the curvature of the ribs of the thorax. The radius of the curvature will vary depending on the size of the patient, with smaller radiuses for smaller patients and larger radiuses for larger patients. The radius of the curvature can range from about 5 cm to about 35 cm depending on the size of the patient. Additionally, the radius of the curvature need not be uniform throughout the canister such that it can be shaped closer to the shape of the ribs. The canister has an active surface, 15 that is located on the interior (concave) portion of the curvature and an inactive surface 16 that is located on the exterior (convex) portion of the curvature. The leads of these embodiments, which are not illustrated except for the attachment port 19 and the proximal end of the lead 21, can be any of the leads previously described above, with the lead illustrated in FIG. 1 being presently preferred.

The circuitry of this canister is similar to the circuitry described above. Additionally, the canister can optionally have at least one sense electrode located on either the active surface of the inactive surface and the circuitry within the canister can be programmable as described above to allow for the selection of the best sense electrodes. It is presently preferred that the canister have two sense electrodes 26 and 28 located on the inactive surface of the canisters as illustrated, where the electrodes are spaced from about 1 to about 10 cm apart with a spacing of about 3 cm being presently preferred. However, the sense electrodes can be located on the active surface as described above.

It is envisioned that the embodiment of FIG. 12 will be subcutaneously implanted adjacent and parallel to the left anterior 5th rib, either between the 4th and 5th ribs or between the 5th and 6th ribs. However other locations can be used.

Another component of the S-ICD of the present invention is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacings to optimize signal detection comparable to the implantable system.

FIGS. 14 to 18 depict particular US-ICD embodiments of the present invention. The various sensing, shocking and pacing circuitry, described in detail above with respect to the S-ICD embodiments, may additionally be incorporated into the following US-ICD embodiments. Furthermore, particular aspects of any individual S-ICD embodiment discussed above may be incorporated, in whole or in part, into the US-ICD embodiments depicted in the following figures.

Figure 14:
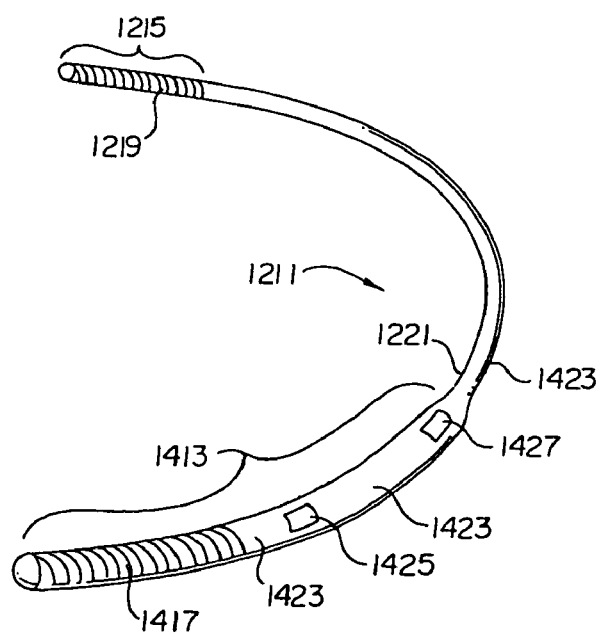
FIG. 14 is a schematic view of a unitary subcutaneous ICD (US-ICD) of the present invention.

Turning now to FIG. 14, the US-ICD of the present invention is illustrated. The US-ICD consists of a curved housing 1211 with a first and second end. The first end 1413 is thicker than the second end 1215. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillating electrodes 1417 and 1219 located on the outer surface of the two ends of the housing. The circuitry can provide cardioversion/defibrillation energy in different types of waveforms. In one embodiment, a 100 uF biphasic waveform is used of approximately 10-20 ms total duration and with the initial phase containing approximately ⅔ of the energy, however, any type of waveform can be utilized such as monophasic, biphasic, multiphasic or alternative waveforms as is known in the art.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way the patient can have a comfortable canister that conforms to the unique shape of the patient's rib cage. Examples of conforming ICD housings are provided in U.S. Pat. No. 5,645,586, the entire disclosure of which is herein incorporated by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 Joules, a feature of the preferred embodiment is that the charge time for the therapy, intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide with about 1 cm being presently preferred. As microtechnology advances, the thickness of the housing will become smaller.

The two cardioversion/defibrillation electrodes on the housing are used for delivering the high voltage cardioversion/defibrillation energy across the heart. In the preferred embodiment, the cardioversion/defibrillation electrodes are coil electrodes, however, other cardioversion/defibrillation electrodes could be used such as having electrically isolated active surfaces or platinum alloy electrodes. The coil cardioversion/defibrillation electrodes are about 5-10 cm in length. Located on the housing between the two cardioversion/defibrillation electrodes are two sense electrodes 1425 and 1427. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 1423. Analogous types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister, or as presently preferred, via the use of a programming wand or via a wireless connection to program the circuitry within the canister.

Figure 15:
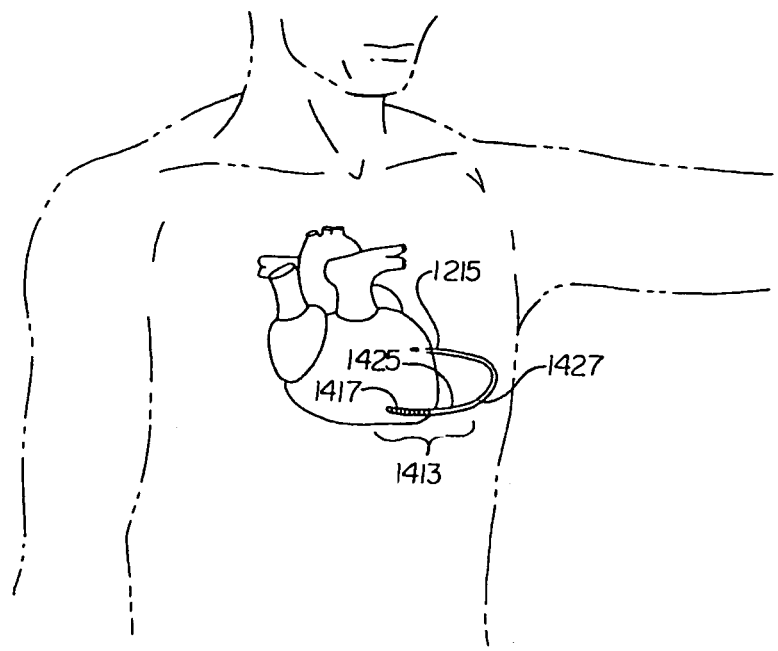
FIG. 15 is a schematic view of the US-ICD subcutaneously implanted in the thorax of a patient.

Turning now to FIG. 15, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the Figures only for help in understanding where the device and its various electrodes are three-dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 16:
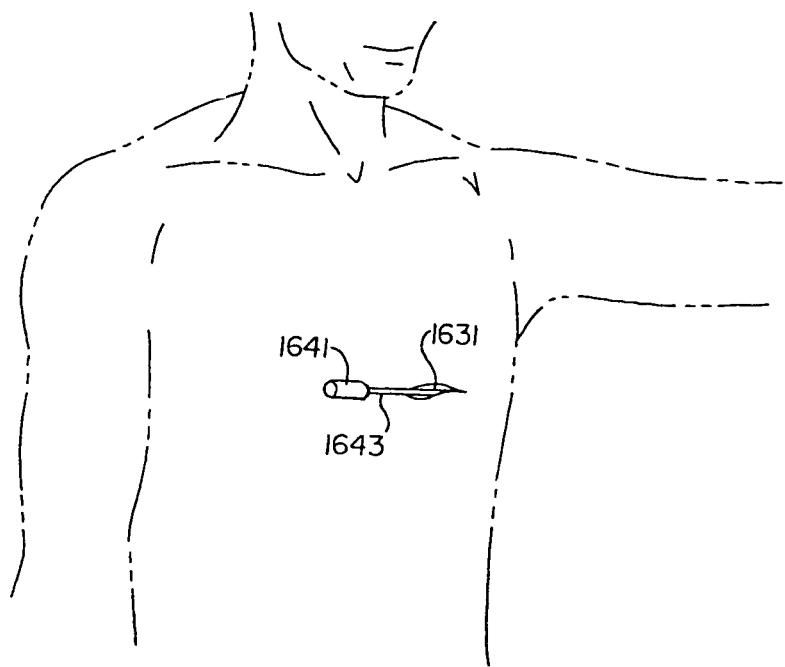
FIG. 16 is a schematic view of the method of making a subcutaneous path from the preferred incision for implanting the US-ICD.
Figure 17:
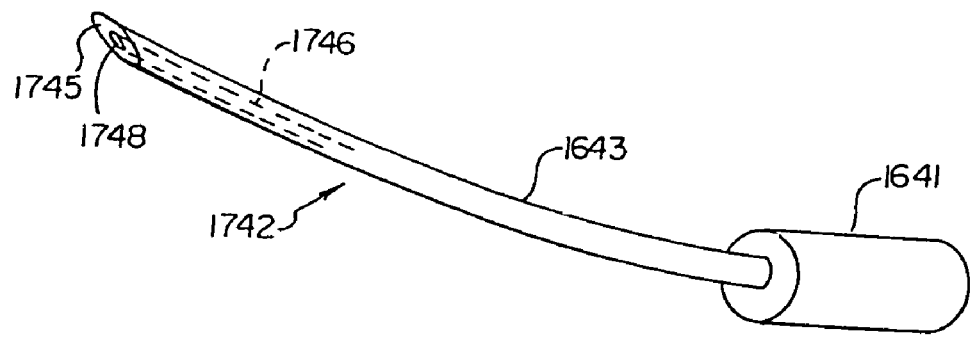
FIG. 17 is a schematic view of an introducer for performing the method of US-ICD implantation.

FIG. 16 schematically illustrates the method for implanting the US-ICD of the present invention. An incision 1631 is made in the left anterior axillary line approximately at the level of the cardiac apex. A subcutaneous pathway is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway is created medially to the inframammary crease and extends posteriorly to the left posterior axillary line. The pathway is developed with a specially designed curved introducer 1742 (see FIG. 17). The trocar has a proximal handle 1641 and a curved shaft 1643. The distal end 1745 of the trocar is tapered to allow for dissection of a subcutaneous path in the patient. Preferably, the trocar is cannulated having a central lumen 1746 and terminating in an opening 1748 at the distal end. Local anesthetic such as lidocaine can be delivered, if necessary, through the lumen or through a curved and elongated needle designed to anesthetize the path to be used for trocar insertion should general anesthesia not be employed. Once the subcutaneous pathway is developed, the US-ICD is implanted in the subcutaneous space, the skin incision is closed using standard techniques.

Figure 18:
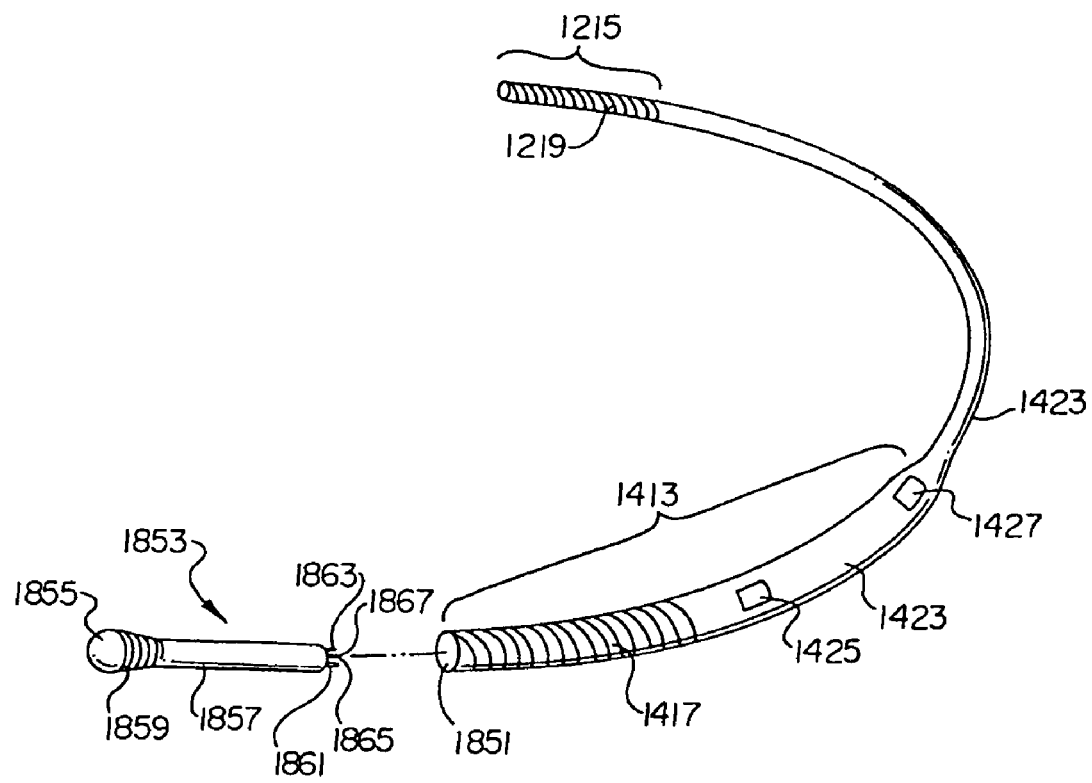
FIG. 18 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 18, a different embodiment is schematically illustrated in exploded view which provides different sized US-ICDs that are easier to manufacture. The different sized US-ICDs will all have the same sized and shaped thick end 1413. The thick end is hollow inside allowing for the insertion of a core operational member 1853. The core member comprises a housing 1857 which contains the battery supply, capacitor and operational circuitry for the US-ICD. The proximal end of the core member has a plurality of electronic plug connectors. Plug connectors 1861 and 1863 are electronically connected to the sense electrodes via pressure fit connectors (not illustrated) inside the thick end, which are standard in the art. Plug connectors 1865 and 1867 are also electronically connected to the cardioverter/defibrillator electrodes via pressure fit connectors inside the thick end. The distal end of the core member comprises an end cap 1855, and a ribbed fitting 1859 which creates a water-tight seal when the core member is inserted into opening 1851 of the thick end of the US-ICD.

The S-ICD and US-ICD, in alternative embodiments, have the ability to detect and treat atrial rhythm disorders, including atrial fibrillation. The S-ICD and US-ICD have two or more electrodes that provide a far-field view of cardiac electrical activity that includes the ability to record the P-wave of the electrocardiogram as well as the QRS. One can detect the onset and offset of atrial fibrillation by referencing to the P-wave recorded during normal sinus rhythm and monitoring for its change in rate, morphology, amplitude and frequency content. For example, a well-defined P-wave that abruptly disappeared and was replaced by a low-amplitude, variable morphology signal would be a strong indication of the absence of sinus rhythm and the onset of atrial fibrillation. In an alternative embodiment of a detection algorithm, the ventricular detection rate could be monitored for stability of the R-R coupling interval. In the examination of the R-R interval sequence, atrial fibrillation can be recognized by providing a near constant irregularly irregular coupling interval on a beat-by-beat basis. An R-R interval plot during AF appears "cloud-like" in appearance when several hundred or thousands of R-R intervals are plotted over time when compared to sinus rhythm or other supraventricular arrhythmias. Moreover, a distinguishing feature compared to other rhythms that are irregularly irregular, is that the QRS morphology is similar on a beat-by-beat basis despite the irregularity in the R-R coupling interval. This is a distinguishing feature of atrial fibrillation compared to ventricular fibrillation where the QRS morphology varies on a beat-by-beat basis. In yet another embodiment, atrial fibrillation may be detected by seeking to compare the timing and amplitude relationship of the detected P-wave of the electrocardiogram to the detected QRS(R-wave) of the electrocardiogram. Normal sinus rhythm has a fixed relationship that can be placed into a template matching algorithm that can be used as a reference point should the relationship change.

In other aspects of the atrial fibrillation detection process, one may include alternative electrodes that may be brought to bear in the S-ICD or US-ICD systems either by placing them in the detection algorithm circuitry through a programming maneuver or by manually adding such additional electrode systems to the S-ICD or US-ICD at the time of implant or at the time of follow-up evaluation. One may also use electrodes for the detection of atrial fibrillation that may or may not also be used for the detection of ventricular arrhythmias given the different anatomic locations of the atria and ventricles with respect to the S-ICD or US-ICD housing and surgical implant sites.

Once atrial fibrillation is detected, the arrhythmia can be treated by delivery of a synchronized shock using energy levels up to the maximum output of the device therapy for terminating atrial fibrillation or for other supraventricular arrhythmias. The S-ICD or US-ICD electrode system can be used to treat both atrial and ventricular arrhythmias not only with shock therapy but also with pacing therapy. In a further embodiment of the treatment of atrial fibrillation or other atrial arrhythmias, one may be able to use different electrode systems than what is used to treat ventricular arrhythmias. Another embodiment would be to allow for different types of therapies (amplitude, waveform, capacitance, etc.) for atrial arrhythmias compared to ventricular arrhythmias.

The core member of the different sized and shaped US-ICD will all be the same size and shape. That way, during an implantation procedure, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

To ensure adequate pacing capture of the heart through an S-ICD having a subcutaneous only lead system, pacing therapy needs to be considerably enhanced by using a biphasic rather than the conventional monophasic waveform for pacing. In addition, to further compensate for the lack of direct contact with the heart, the subcutaneous electrode system, especially the anterior thoracic electrode system, that will be delivering the ATP stimuli should result in as high as a current density as possible in order to activate the cardiac tissues. This can be facilitated by using a small electrode as close to the sternum as possible in the tissues overlying the right ventricle, the cardiac chamber closest to the anterior subcutaneous space where the S-ICD of the present invention will lie.

Figure 19:
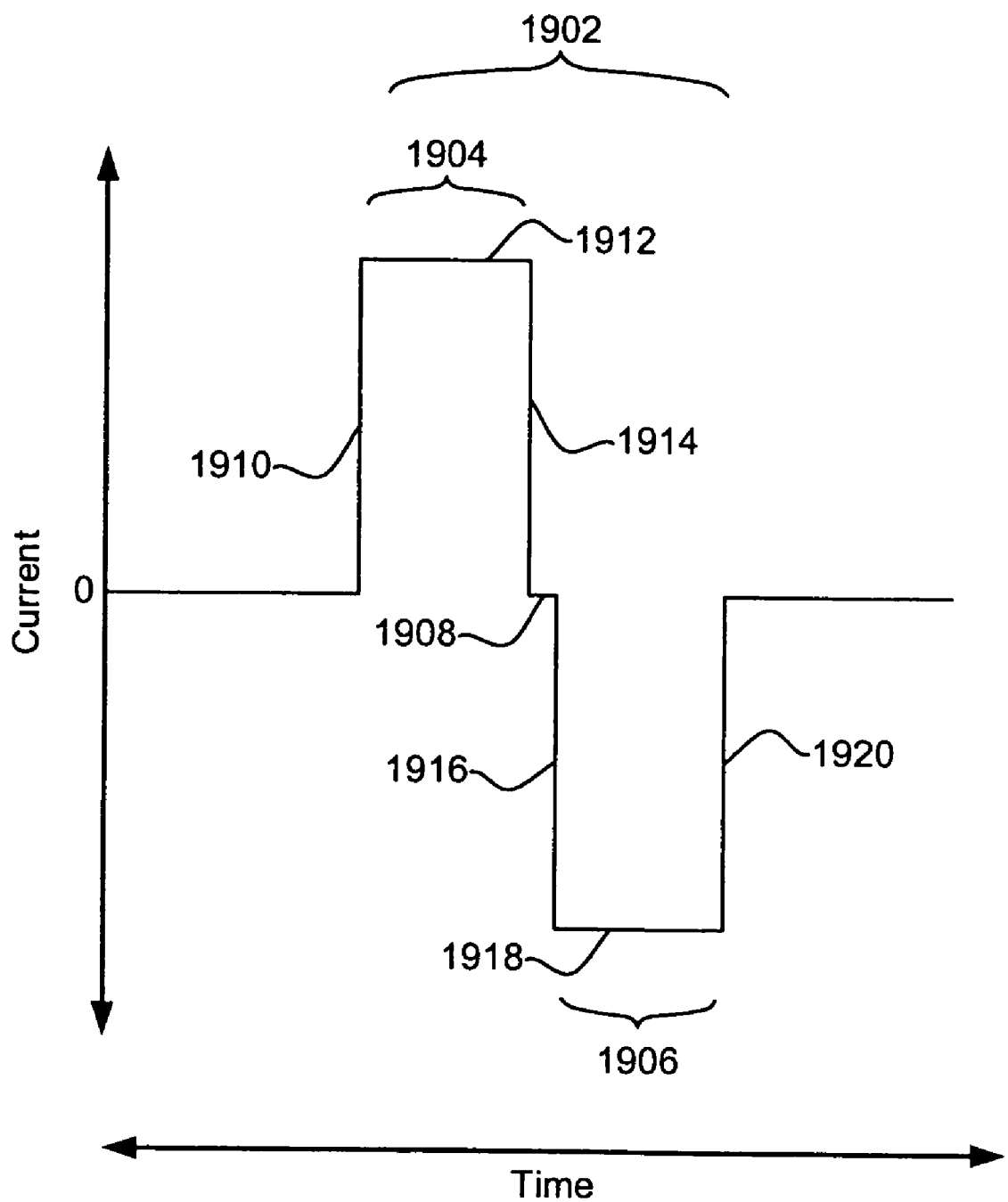
FIG. 19 is a graph that shows an example of a biphasic waveform for use in anti-tachycardia pacing in an embodiment of the present invention.

FIG. 19 is a graph that shows an embodiment of the example of a biphasic waveform for use in anti-tachycardia pacing applications in subcutaneous implantable cardioverter-defibrillators ("S-ICD") in an embodiment of the present invention. As shown in FIG. 19, the biphasic waveform is plotted as a function of current versus time.

In an embodiment, the biphasic waveform 1902 comprises a positive portion 1904, a negative portion 1906 and a transition portion 1908. In an embodiment, both the positive portion 1904 and the negative portion 1906 are substantially rectangular in shape. The positive portion 1904 of the biphasic waveform 1902 comprises an initial positive current 1910, a positive fixed current 1912 and a final positive current 1914. The negative portion 1906 of the biphasic waveform 1902 comprises an initial negative current 1916, a negative fixed current 1918 and a final negative current 1920. In an embodiment, the polarities of the biphasic waveform 1902 can be reversed such that the negative portion 1906 precedes the positive portion 1904 in time.

As shown in FIG. 19, the biphasic waveform 1902 is initially at zero current. Upon commencement of the anti-tachycardia pacing, a current of positive polarity is provided and the biphasic waveform 1902 rises to the initial positive current 1910. Next, the current of the biphasic waveform 1902 remains at a constant level along the positive fixed current 1912. The positive portion 1904 of the biphasic waveform 1902 is then truncated and a negative current is provided. The biphasic waveform 1902 then undergoes a relatively short transition portion 1908 where the current is approximately zero. Next, the biphasic waveform 1902 is increased (in absolute value) in the opposite (negative) polarity to the initial negative current 1916. After reaching its maximum negative current (in absolute value), the current of the biphasic waveform 1902 remains at a constant level along the negative fixed current 1918. After the negative portion 1906 of the biphasic waveform 1902 is truncated at the final negative current 1914, the biphasic waveform 1902 returns to zero.

The total amount of time that the biphasic waveform 1902 comprises is known as the "pulse width." In an embodiment, the pulse width of the biphasic waveform can range from approximately 1 millisecond to approximately 40 milliseconds. The total amount of energy delivered is a function of the pulse width and the absolute value of the current.

An example of one embodiment of the biphasic waveform 1902 will now be described. In this embodiment, the amplitude of the initial positive current 1910 can range from approximately one to approximately 250 milliamps. Similarly, the amplitude of the initial negative current 1916 can range from approximately one to approximately 250 milliamps.

In the example, the pulse width of the biphasic waveform 1902 can range from approximately 1 millisecond to approximately 40 milliseconds. In addition, the implantable cardioverter-defibrillator employs biphasic anti-tachycardia pacing at rates of approximately 20 to approximately 120 stimuli/minute for severe bradycardia episodes, although programming of higher pacing rates up to 120 stimuli/minute is also possible.

Figure 20:
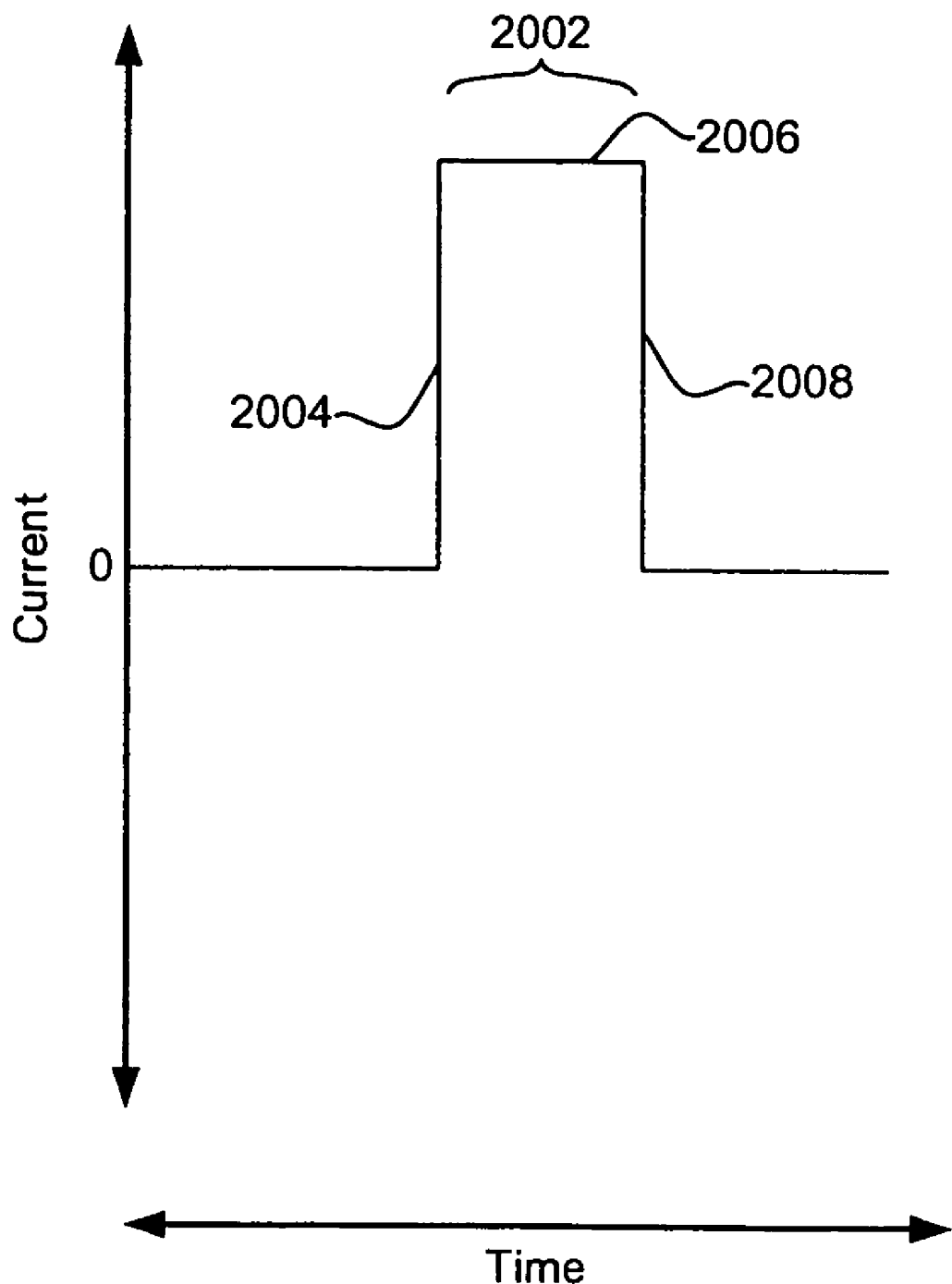
FIG. 20 is a graph that shows an example of a monophonic waveform for use in anti-tachycardia pacing in an embodiment of the present invention.

FIG. 20 is a graph that shows an embodiment of the example of a monophasic waveform for use in anti-tachycardia pacing applications in subcutaneous implantable cardioverter-defibrillators ("S-ICD") in an embodiment of the present invention. As shown in FIG. 20, the monophasic waveform is plotted as a function of current versus time.

In an embodiment, the monophasic waveform 2002 comprises an initial positive current 2004, a positive fixed current 2006 and a final positive current 2008. In an embodiment, the monophasic waveform 2002 is substantially rectangular in shape. In an embodiment, the polarities of the monophasic waveform 2002 can be reversed such that the waveform 2002 is negative in polarity.

As shown in FIG. 20, the monophasic waveform 2002 is initially at zero current. Upon commencement of the anti-tachycardia pacing, a current of positive polarity is provided and the monophasic waveform 2002 rises to the initial positive current 2004. Next, the current of the monophasic waveform 2002 remains at a constant level along the positive fixed current 1906. The monophasic waveform 2002 is then truncated.

An example of one embodiment of the monophasic waveform 2002 will now be described. In this embodiment, the amplitude of the initial positive current 2004 can range from approximately one to approximately 250 milliamps.

In an embodiment, the pulse width of the biphasic waveform 2002 can range from approximately 1 millisecond to approximately 40 milliseconds. In addition, the implantable cardioverter-defibrillator employs anti-tachycardia pacing at rates of approximately 100 to approximately 350 stimuli/minute for ventricular tachycardia episodes. In addition, up to 30 ATP stimuli for any single attempt could be allowed and as many as 15 ATP attempts could be allowed for any effort to terminate a single episode of VT. One might also allow for different ATP methods to be employed for VTs of different rates or ECG characteristics. Moreover, the device may be allowed to auto-select the method of ATP to be used based upon the device's and/or the physician's experience with previous episodes of VT or with the patient's underlying cardiac condition. In order to maintain these rates, in one embodiment of the invention, the power supply continues to operate to maintain a sufficient voltage to deliver a constant current.

Although it possible for the present invention to provide standard ATP at predetermined or preprogrammed rates for monomorphic VT, the use of an S-ICD may also be employed for the treatment of other arrhythmias such as atria tachyarrhythmias. In another embodiment, the invention can provide ATP in response to a certain activity, respiration, pressure or oxygenation sensor as coupled to arrhythmia characteristics.

The S-ICD and US-ICD devices and methods of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What we claim is:

1. A method of treatment of a patient comprising:
   implanting a cardiac stimulus device consisting of a canister and a lead, the canister including one or more electrodes thereon, the lead including a stimulus delivery electrode, such that the cardiac stimulus device, once implanted is entirely disposed in non-vascular and non-cardiac locations;
   wherein implantation is performed such that the cardiac stimulus device senses cardiac signals in order to identify an arrhythmia using at least one electrode on the lead in combination with at least one electrode on the canister, with neither electrode that is used for sensing disposed in or on the heart of the patient; and
   wherein implantation is performed such that the cardiac stimulus device will, in response to a detected arrhythmia, deliver defibrillation therapy to the heart of the patient using only the stimulus delivery electrode of the lead and an electrode disposed on the canister, such that therapy will be delivered with neither therapy delivery electrode disposed in or on the heart of the patient.

2. The method of claim 1, wherein the stimulus delivery electrode is a coil electrode.

3. The method of claim 1, wherein the stimulus delivery electrode is a coil electrode having a length of about 5-10 cm.

4. The method of claim 1, wherein the canister and the lead are implanted such that neither extends beneath the ribs.

5. The method of claim 1, wherein the canister and the lead are implanted such that each is disposed at non-intra-thoracic locations.

6. The method of claim 1, wherein implantation is performed such that the cardiac stimulus device senses cardiac signals in order to identify a need for pacing therapy using only electrodes that neither contact nor enter the heart of the patient, and, when a need for pacing therapy is identified, the cardiac stimulus device delivers a series of electrical impulses, including timing the delivery of the series of electrical impulses in a manner achieving a pacing function.

7. The method of claim 1, wherein the stimulus delivery electrode is a longitudinally extending coil electrode disposed outside the ribs and disposed in a generally linear fashion, on the anterior chest of the patient.

8. A method of treatment of a patient comprising:
   implanting a cardiac stimulus device consisting of a canister housing stimulus delivery circuitry and a lead including one or more electrodes, such that, once implanted, the cardiac stimulus device is entirely disposed in non-vascular and non-cardiac locations;

wherein implantation is performed such that the cardiac stimulus device senses cardiac signals in order to identify an arrhythmia using at least one electrode on the lead in combination with at least one electrode on the canister, with neither electrode that is used for sensing disposed in or on the heart of the patient; and wherein the implantation is performed such that the cardiac stimulus device, upon identifying an arrhythmia, will use the stimulus delivery circuitry to deliver defibrillation therapy using a first single electrode and a second single electrode, both electrodes being disposed outside the patient's heart and vasculature;

wherein the stimulus delivery circuitry generates an output current between only the first single electrode and the second single electrode, wherein the first electrode is disposed on the lead and the second electrode is disposed on the canister.

9. The method of claim 8, wherein at least one of the first single electrode and/or the second single electrode is a coil electrode.

10. The method of claim 8, wherein at least one of the first single electrode and/or the second single electrode is a coil electrode having a length of about 5-10 cm.

11. The method of claim 8, wherein each of the first single electrode and the second single electrode are implanted such that neither extends beneath the ribs of the patient.

12. The method of claim 8, wherein each of the first single electrode and the second single electrode are implanted such that each is disposed in the patient at non-intra-thoracic locations.

13. The method of claim 8, wherein the implantation is performed such that the cardiac stimulus device also senses cardiac signals to determine whether there is a need for pacing therapy and, upon identifying a need for pacing therapy, will use the stimulus delivery circuitry to deliver, via the first single electrode and the second single electrode, a series of electrical impulses, wherein the method also includes timing the delivery of the series of electrical impulses in a manner achieving a pacing function.

14. The method of claim 8, wherein the defibrillation therapy has a biphasic waveform.

15. A method of treatment comprising:

implanting in a patient a cardiac stimulus device consisting of a canister and a lead electrode assembly, the canister housing output circuitry for providing output electrical stimulus to the patient between first and second outputs, a first stimulus electrode disposed on the lead electrode assembly, the first output being coupled to the first stimulus electrode and no other electrode, the second output being coupled to one or more stimulus electrodes disposed on the canister and no other electrode, the cardiac stimulus device being implanted such that no part thereof extends into or resides within the thoracic cavity of the patient;

wherein the implantation is performed such that the cardiac stimulus device, once implanted, will sense cardiac electrical activity in order to detect arrhythmias using only electrodes that are implanted without contacting or entering the heart of the patient; and wherein the implantation is performed such that the cardiac stimulus device, upon identifying an arrhythmia, will use the stimulus delivery circuitry to deliver defibrillation therapy to the patient via the output circuitry by using only electrodes that do not contact or enter the heart of the patient.

16. The method of claim 15, wherein the output circuitry is adapted to reverse the polarity of the first and second outputs to generate a biphasic waveform.

17. The method of claim 15, wherein the first stimulus electrode is a coil electrode having a length of about 5-10 cm.

* * * * *